United States Patent [19]
Yeh et al.

[11] Patent Number: 5,183,053
[45] Date of Patent: Feb. 2, 1993

[54] ELLIPTICAL BIOPSY PUNCH

[75] Inventors: Charles R. Yeh, Plantation, Fla.; Donald H. Huldin, Okemos, Mich.

[73] Assignee: Acuderm, Inc., Ft. Lauderdale, Fla.

[21] Appl. No.: 685,466

[22] Filed: Apr. 12, 1991

[51] Int. Cl.⁵ .............................................. A61B 10/00
[52] U.S. Cl. ........................................ 128/754; 606/167
[58] Field of Search ...................... 128/749, 751, 754; 606/167, 170, 172

[56] References Cited

U.S. PATENT DOCUMENTS

| | | | |
|---|---|---|---|
| 2,690,750 | 10/1954 | Steinberg | 606/167 |
| 3,512,519 | 5/1970 | Hall | 128/754 |
| 3,577,979 | 5/1971 | Gaast | 128/754 |
| 3,990,451 | 11/1976 | Gibbs | 128/754 |
| 4,007,732 | 2/1977 | Kvale et al. | 128/754 |
| 4,059,115 | 11/1977 | Jamashev et al. | 606/172 |
| 4,099,518 | 7/1978 | Bayliss et al. | 128/754 |
| 4,649,918 | 3/1987 | Pegg et al. | 128/754 |
| 4,832,045 | 5/1989 | Goldbeyer | 128/754 |

FOREIGN PATENT DOCUMENTS 3525917  2/1986  Fed. Rep. of Germany ...... 606/167

*Primary Examiner*—Max Hindenburg
*Attorney, Agent, or Firm*—Rockey, Rifkin & Ryther

[57] ABSTRACT

The disposable punch of the present invention is of a simple two-piece construction where the first piece is a molded plastic handle portion having an elongated shape designed to be grasped by the surgeon. The handle portion terminates in a receptacle which receives the blade of the biopsy punch. In cross-section, the blade has an elliptical shape and terminates in a cutting edge that lies in a single plate. The blade is force fit into the receptacle of the handle portion and is maintained in this position by a friction fit.

7 Claims, 1 Drawing Sheet

ELLIPTICAL BIOPSY PUNCH

BACKGROUND OF THE INVENTION

The present invention relates generally to surgical instruments and, more particularly, to an elliptical skin biopsy punch. As is well-known in the art, abnormalities found on the surface of the skin, such as tumors or lesions, are removed by a simple surgical procedure for further examination and analysis. Traditionally, this surgical procedure was performed "free-hand" by a surgeon using a scalpel. An incision was made around the skin abnormality to create an isolated piece of skin that was lifted by forceps to expose the underlying tissue. The tissue would then be cut away by a scalpel or scissors such that the abnormality could be removed. Typically, an elliptical incision was made about the skin abnormality so that the wound would heal with the least amount of visible scarring. The elliptical incision also accelerated the healing process because the exposed surfaces of the wound could be evenly joined together with a minimum stretching of the skin.

While such a surgical procedure was relatively simple, it was difficult for the surgeon to make precise elliptical incisions around the skin abnormality such that the healing benefits provided by an elliptical incision were not always realized. In an attempt to obviate this problem, surgical incision guides were devised. One such example of a guide is shown in U.S. Pat. No. 4,192,312 issued to Wilson. Wilson shows a patch of material which acts as a template and is placed over the skin abnormality so as to guide the scalpel while the surgeon made the free-hand incision. While such a device lessened the problems associated with free-hand incisions, making precise cuts was still dependent on the skill of the individual surgeon. Moreover, the incision guides did nothing to insure that the scalpel cut at a uniform depth such that removed tissue had a uniform thickness. Obtaining a tissue sample of uniform thickness is critical for the performance of pathological analysis and diagnosis.

As a result, skin biopsy punches were developed which could consistently make a uniform incision around a skin abnormality. One such skin biopsy punch, also referred to as a circular punch, contained an incision blade which was circular in shape. Such circular punches, when used to remove skin lesions, created an oval-like defect after use. If the oval-like defect was sufficiently small, the wound would be allowed to heal. However, larger incisions would require closure which would result in "dog ears" on each of the oval ends of the defect. The surgeon would be required to notch the oval ends of the defect, creating a linear defect which could then be closed by suture or staple. A circular skin biopsy punch is shown in U.S. Pat. No. 3,515,128 issued to McEvoy.

In U.S. Pat. No. 3,990,451, issued to Gibbs, a surgical instrument for removing skin lesions having a navicular shape was developed. However, the incision blade of Gibbs is difficult to manufacture because it has a complex convex cutting edge. Moreover, the Gibbs device is difficult to use because the surgeon must rock the convex cutting head across the surface of the skin to make the incision. The shape of the cutting head and the required rocking action make it difficult to remove a specimen having a uniform thickness as the specimen will be thicker at its middle than at its ends. Thus, an elliptical biopsy punch that has a simpler and less expensive construction and is simpler to use than the Gibbs device is desired.

BRIEF DESCRIPTION OF THE INVENTION

The biopsy punch of the present invention overcomes the above-noted shortcomings by providing a punch that is simple and economical to manufacture and easy to use. The disposable punch of the present invention is of a simple two-piece construction where the first piece is a molded plastic handle portion having an elongated shape designed to be grasped by the surgeon. The handle portion terminates in a receptacle which receives the blade of the biopsy punch. In cross-section, the blade has an elliptical shape and terminates in a razor sharp cutting edge that lies in a single plane. The blade is force fit into the receptacle of the handle portion and is maintained in this position by a friction fit. The biopsy punch of the present invention has a simple and economical construction, yet provides a consistent elliptical incision of uniform depth. Because of the simplicity of the design of the invention, the biopsy punch is inexpensive to manufacture and, therefore, can be disposed of after use.

OBJECTS OF THE INVENTION

It is a general object of the invention to provide an improved elliptical biopsy punch.

It is another object of the invention to provide an elliptical biopsy punch that makes an incision of constant and uniform depth to provide a tissue specimen having a uniform thickness for accurate diagnosis.

It is a further object of the invention to provide a biopsy punch that facilitates the closing of the wound and minimizes scarring.

It is yet another object of the invention to provide a biopsy punch having a simple and economical design.

It is a further object of the invention to provide a biopsy punch that is inexpensive to manufacture such that it can be made disposable.

It is still a further object of the invention to provide an elliptical biopsy punch having a blade that makes the surgical procedure simple to perform.

Other objects of the invention, in addition to those set forth above, will become apparent to one of ordinary skill in the art from the following detailed description of the invention.

DETAILED DESCRIPTION OF THE INVENTION

Figure 1:
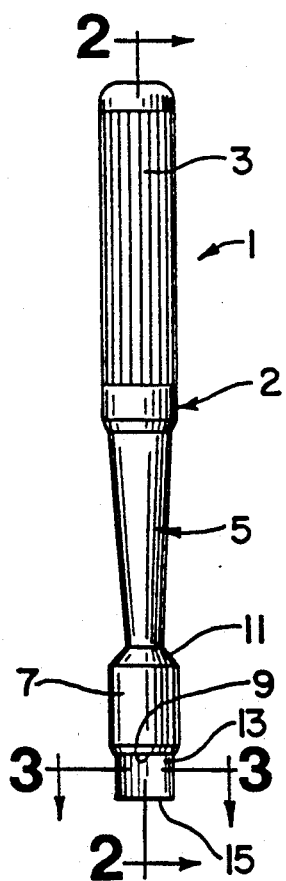
FIG. 1 shows a side view of the biopsy punch of the invention.
Figure 2:
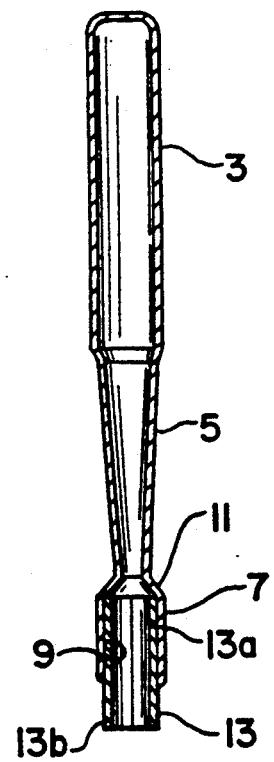
FIG. 2 shows a longitudinal section view of the biopsy punch of the invention.

Referring more particularly to FIGS. 1 and 2, the biopsy punch of the invention 1 consists of a handle portion 2 formed of a rigid plastic material. Handle portion 2 includes an upper section 3 having ridges formed thereon which enhance the surgeon's grip. A middle section 5 having a smooth outer surface joins the upper section 3 to a lower section 7. Lower section 7 includes an enlarged cylindrical receptacle 9 such that a rim 11 is formed where the surgeon can apply pressure to perform the punching operation. Handle 3 is made hollow to form passage 4 and has an aperture 6 formed at the top thereof allowing access to the interior of the punch. Passage 4 is provided to allow the surgeon to push the specimen out of the blade 13 from the inside, if necessary.

Figure 3:
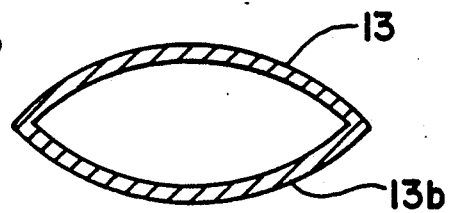
FIG. 3 is a section view of the blade of the biopsy punch of the invention, taken along line 3—3 of FIG. 1.

Referring more particularly to FIGS. 1, 2 and 3, surgical blade 13 has a first portion 13a of generally annular cross-section disposed within receptacle 9 and a second portion 13b having an elliptical cross-section. Blade 13 is composed of surgical steel and is dimensioned such that a tight friction fit results between first portion 13a and receptacle 9 to retain the blade in the handle portion 2. It will be appreciated that a mechanical connection can be used to join the blade 13 and handle portion 2 rather than a friction fit. For example, the plastic handle could be integrally formed over a portion of the blade 13 during the manufacturing process. The razor sharp cutting edge 15 of blade 13 has an elliptical profile as shown most clearly in FIG. 3. Moreover, the second portion 13b extends from the receptacle a uniform distance such that the cutting edge 15 is disposed in a plane perpendicular to the longitudinal axis of handle 3 and, in side view, forms a straight line. It will be understood by one of ordinary skill in the art that the elliptical cutting edge can be dimensioned as required so as to circumscribe skin abnormalities of various sizes.

To construct the biopsy punch of the invention, the handle portion 2 is first extruded from a rigid plastic material as is well known in the art. The preformed blade 13 is then press fit into receptacle 9 to form an integral unit therewith. As is evident from the foregoing description, the construction and assembly of the punch of the invention is simple and inexpensive. As a result, punch 1 can be disposed of after use such that a new sterile punch can be used for each surgical procedure.

In operation, the cutting edge 15 of blade 13 is placed on the skin such that it circumscribes the skin abnormality that is to be removed. A substantially downward force is applied to the blade by the surgeon via rim 11 such that the cutting edge 15 severs the skin surrounding the abnormality to create an incision having a uniform depth. A slight vibration motion may be employed to create the incision, if necessary. The surgeon then cuts the severed tissue from the tissue underlying it so the specimen can be removed and analyzed. As is evident from the foregoing description, the resulting incision will have a generally elliptical shape such that the joining of the opposite sides of the incision to one another can be done easily with a minimal amount of stretching of the skin or deformation of the incision. Thus, the punch of the invention allows the surgeon to quickly and easily perform the biopsy incision while minimizing scarring effects and facilitating the healing of the wound. Moreover, because the punch consistently creates to an incision having a uniform depth, the biopsy specimen removed will be of better quality and undercutting of the biopsy specimen will be minimized.

While the embodiments of this invention have been shown and described in some detail, it will be understood that this description and the accompanying drawings are offered merely by way of example, and that the invention is to be limited in scope only by the appended claims.

What is claimed is:

1. A disposable surgical instrument in the form of a biopsy punch for making an elliptical incision in the skin to remove skin abnormalities, comprising:
   (a) an elongated handle member formed of a hard plastic material including a means for retaining a cutting member formed integrally on one end of said handle member; and
   (b) a cutting member retained by said retaining means and projecting therefrom to expose a cutting surface for making the incision, said cutting member having a first and second portion, said first portion being disposed within said retaining means and being substantially annular in cross-section and said second portion being generally elliptical in cross-section.

2. The surgical instrument according to claim 1, wherein said cutting member extends a uniform distance from said means for retaining.

3. The surgical instrument according to claim 1, wherein said retaining means includes a receptacle dimensioned to receive said cutting member.

4. The surgical instrument according to claim 1, wherein said cutting member is composed of surgical steel.

5. The surgical instrument according to claim 1, wherein said first portion of the cutting member is force fit and frictionally retained within said retaining means.

6. The surgical instrument of claim 1, wherein said cutting surface is formed on the second portion and consists of a razor sharp blade.

7. The surgical instrument according to claim 1, wherein said elongated handle member is formed with a rim for receiving the punching force.

* * * * *